United States Patent [19]

Okuda et al.

[11] Patent Number: 5,710,323
[45] Date of Patent: Jan. 20, 1998

[54] PROCESS FOR PRODUCING MONOCARBOXYLIC AND/OR DICARBOXYLIC ACIDS

[75] Inventors: Ryoichi Okuda; Tadashi Kato; Yoshio Okada, all of Tokuyama, Japan

[73] Assignee: Idemitsu Petrochemical Co., Ltd., Tokyo, Japan

[21] Appl. No.: 809,701

[22] PCT Filed: Jul. 20, 1995

[86] PCT No.: PCT/JP95/01444

§ 371 Date: Mar. 27, 1997

§ 102(e) Date: Mar. 27, 1997

[87] PCT Pub. No.: WO96/10006

PCT Pub. Date: Apr. 4, 1996

[30] Foreign Application Priority Data

Sep. 29, 1994 [JP] Japan .................. 6-235724
Apr. 13, 1995 [JP] Japan .................. 7-088192

[51] Int. Cl.$^6$ .................................. C07C 51/10
[52] U.S. Cl. ............... 562/497; 560/204; 562/521
[58] Field of Search ........................... 562/497, 521; 560/204

[56] References Cited

U.S. PATENT DOCUMENTS 3,965,132  6/1976  Norell ........................... 260/410.9
5,034,398  7/1991  Drent ............................... 502/168

OTHER PUBLICATIONS

Booth, J. C. S. Perkin I, pp. 2441–2446, 1979.
Farooq, J Am. Chem. Soc., vol. 110, pp. 864–867, 1988.

*Primary Examiner*—Michael L. Shippen
*Attorney, Agent, or Firm*—Antonelli, Terry, Stout & Kraus, LLP

[57] ABSTRACT

A process for producing a monocarboxylic acid and/or a dicarboxylic acid by the reaction of a starting compound selected from among saturated hydrocarbons, α-olefins of 6 to 20 carbon atoms, saturated monocarboxylic acids and esters of the acids either with both of carbon monoxide and water at the same time or first with carbon monoxide and then with water, wherein the reaction of the starting compound either with both of carbon monoxide and water or with carbon monoxide alone is conducted in a strong acid solution containing a trifluoromethane-sulfonic acid catalyst and an alcohol and/or an olefin of 3 to 5 carbon atoms.

14 Claims, No Drawings

PROCESS FOR PRODUCING MONOCARBOXYLIC AND/OR DICARBOXYLIC ACIDS

TECHNICAL FIELD

The present invention relates to processes for producing monocarboxylic acids and/or dicarboxylic acids, particularly, to processes for producing a good yield of monocarboxylic acids and/or dicarboxylic acids by the reaction of compounds selected from saturated hydrocarbons, saturated monocarboxylic acids and saturated monocarboxylic esters with carbon monoxide and water.

BACKGROUND ART

Production of carboxylic acids by the reaction of alcohols or olefins with carbon monoxide in strong acids, such as sulfuric acid, followed by hydrolysis with water is called the Koch's reaction or the Koch-Harf reaction and has been widely applied for a long time. In a recent application (variation) of the Koch's reaction, saturated hydrocarbons are used as starting materials instead of alcohols or olefins to obtain useful carboxylic acids or mixtures thereof from various saturated hydrocarbons or petroleum distillates of lower value. Strictly speaking, the reaction of saturated hydrocarbons with carbon monoxide and water to produce carboxylic acids is not the so-called Koch's reaction, but is often called the Koch's reaction of saturated hydrocarbons (the Koch's reaction in a broader sense) because of the similarity in reaction.

The marked difference between the so-called Koch's reaction using as starting materials alcohols or olefins and the Koch's reaction in a broader sense is the difference in the reactivity of the starting materials.

The former Koch's reaction is rarely restricted in starting materials and catalysts, since alcohols and olefins of 3 or more carbon atoms, whether normally linear, branched or cyclic, are so reactive as to easily form alkyl cations, and various strong acid catalysts are effective as catalysts. Industrially common catalysts are of sulfuric acid systems because of their high activity and low cost. The use of sulfuric acid, however, gives product carboxylic acids contaminated with sulfur and tends to cause emission of an offensive odor. Therefore, development of new catalysts has been an important problem for the prevention or reduction of such an offensive odor rather than for the improvement of activity. For example, in Japan Patent Application Unexamined Publication No. 62-164645 are proposed catalysts comprising sulfuric acid and phosphoric acid as catalysts which reduce the offensive odor due to the contamination of the product carboxylic acids with sulfur. As an example of the Koch's reaction of alcohols or olefins using catalysts containing no sulfuric acid, a reaction using as a catalyst trifluoromethane-sulfonic acid, which is an organic super acid, is proposed (J. C. S. Parkin I, 1979, p2441).

To the contrary, the Koch's reaction of saturated hydrocarbons is severely restricted in reaction materials since the reactivity of saturated hydrocarbons is low and varies widely depending on structures, and the catalysts therefor also involve many technical problems to be solved.

For example, it is known to produce carboxylic acid by the Koch's reaction of saturated hydrocarbons with carbon monoxide in the coexistence of catalysts comprising sulfuric acid and metal compounds with olefins or alcohols as agents generating alkyl cations (Japan Patent Application Examined Publication Nos. 52-8285 and 52-8286). The method, however, has the considerable defect that the catalysts of low acidity cause the synthesis of carboxylic acids from saturated hydrocarbons containing tertiary hydrogen atoms, but hardly from saturated hydrocarbons containing no tertiary hydrogen atoms.

It is also reported that carboxylic acids can be synthesized even from saturated hydrocarbons containing no tertiary hydrogen atoms by using super acid catalysts, which are called "Magic Acids" and are mixtures of strong acids and Lewis acids such as $HF-SbF_5$ (Chem. Lett., 1983, p17). These catalysts, however, are extremely corrosive and inapplicable to industrial uses.

The above-described trifluoromethane-sulfonic acid ($CF_3SO_3H$) is a super acid, but generally cannot cause synthesis of carboxylic acids from saturated hydrocarbons at atmospheric pressure. The only known synthesis of carboxylic acids by the trifluoromethane-sulfonic acid-catalyzed Koch's reaction of saturated hydrocarbons with carbon monoxide is the synthesis of carboxylic acids from adamantane at high pressures of 8 MPa or higher [J. Am. Chem. Soc., Vol. 110, p 864 (1988)]. Adamantane is known to be a saturated hydrocarbon which has many tertiary hydrogen atoms of high reactivity.

As to the processes for producing dicarboxylic acids by the Koch's reaction, it is known to use catalysts comprising sulfuric acid and metal compounds and, as starting materials, dienes, diols or monocarboxylic acids containing unsaturated bonds (Japan Patent Application Examined Publication Nos. 53-15049 and 53-15050). However, this process is not suitable for industrial production, since the starting materials are hardly available.

DESCRIPTION OF THE INVENTION

The present invention has been made in consideration of the above-described circumstances.

The object of the present invention is to provide practically useful processes for producing monocarboxylic acids and/or dicarboxylic acids, which afford even under mild conditions at around atmospheric pressure at around room temperature a good yield of various monocarboxylic acids and/or dicarboxylic acids from saturated hydrocarbons, saturated monocarboxylic acids and saturated monocarboxylic esters which contain alkyl groups with no tertiary hydrogen atoms, to say nothing of such compounds containing tertiary hydrogen atoms.

As a result of studies for attaining the object of the present invention, we have found that by conducting the Koch's reaction of starting compounds selected from saturated hydrocarbons, saturated monocarboxylic acids and saturated monocarboxylic esters with carbon monoxide, in a strong acid solution wherein trifluoromethane-sulfonic acid catalyst coexists with alcohols and/or olefins, various monocarboxylic acids and/or dicarboxylic acids can be obtained in a good yield even under mild conditions at around atmospheric pressure at around room temperature not only from compounds containing tertiary hydrogen atoms but also from compounds which contain alkyl groups with no tertiary hydrogen atoms, such as straight-chain alkyls or cyclohexyl, and the problems of the corrosion of apparatuses by catalysts or the offensive odor due to impurities, such as sulfur, can also be solved. On the basis of these findings, we have completed the present invention.

That is, the present invention provides a process for producing a monocarboxylic acid and/or a dicarboxylic acid by a reaction of a starting compound selected from the group consisting of a saturated hydrocarbon, a saturated monocarboxylic acid and a saturated monocarboxylic ester either with both of carbon monoxide and water at the same time or first with carbon monoxide and then with water, wherein the reaction of the starting compound either with both of carbon monoxide and water or with carbon monoxide alone is conducted in a strong acid solution containing at least trifluoromethane-sulfonic acid catalyst and an alcohol and/ or an olefin of 3 to 5 carbon atoms.

BEST MODE FOR CARRYING OUT THE INVENTION

In the process of the present invention, the saturated hydrocarbons which may be used as the starting compounds are not particularly limited, and, in general, any kind and any structure of saturated hydrocarbons may be used. Saturated hydrocarbons includes those of various structures, for example, aliphatic alkanes, such as straight-chain alkanes and branched alkanes, including isoalkanes and neoalkanes, alicyclic saturated hydrocarbons, such as cycloalkanes with no branches, including cyclohexane, and branched cycloalkanes, including methylcyclopentane, and polycyclic saturated hydrocarbons, such as decalin and adamantane, all of which may be used as the starting saturated hydrocarbons whether they contain tertiary hydrogen atoms or not.

Among these saturated hydrocarbons of various structures that are suitable for smooth reaction are those containing 4 to 20 carbon atoms, preferably 8 to 20 carbon atoms, and being liquid at room temperature. Saturated hydrocarbons which are solid at room temperature but can be liquefied by mixing with other components may also be used suitably. Such saturated hydrocarbons which are solid at room temperature may also become applicable to the reaction by liquefying them by raising the reaction temperature, but the temperature rise decreases the meltage of carbon monoxide and tends to retard the reaction.

To produce dicarboxylic acids, it is preferable to use as starting compounds saturated hydrocarbons of 10 to 20 carbon atoms, since they facilitate the preparation of dicarboxylic acids. Saturated hydrocarbons of 7 or less carbon atoms sometimes fail to form dicarboxylic acids.

The main products of the reaction using saturated hydrocarbons as starting materials are monocarboxylic acid containing one more carbon atom than the saturated hydrocarbons and/or dicarboxylic acid containing two more carbon atoms than the saturated hydrocarbons, namely, monocarboxylic acids with one carboxyl group introduced and/or dicarboxylic acids with two carboxyl groups introduced. The use of saturated hydrocarbons as the starting compounds generally gives saturated carboxylic acids.

Typical but nonlimitative examples of the Saturated hydrocarbons to be used as the starting compounds are n-alkanes, such as butane, pentane, hexane, heptane, octane, nonane, decane, undecane, dodecane, tridecane, tetradecane, pentadecane, hexadecane, heptadecane, octadecane, nonadecane, icosane, docosane and tricosane, various branched alkanes, such as isobutane, isopentane, isohexane, neohexane, isoheptane, isooctane, isononane, isodecane, isoundecane, isododecane, isotridecane, isotetradecane, isopentadecane, isohexadecane, isoheptadecane, isooctadecane, isononadecane, isoicosane, isodocosane and isotricosane, and various alicyclic alkanes, such as cyclopentane, cyclohexane, cycloheptane, cyclooctane, cyclodecane, cyclododecane, methylcyclopentane, methylcyclohexane, dimethylcyclopentane, dimethylcyclohexane, ethylcyclohexane, propylcyclohexane, isopropylcyclohexane, octylcyclohexane, decalin, adamantane and methyladamantane.

The saturated monocarboxylic acids which may be used as the starting compounds are not particularly limited, and are, for example, straight-chain saturated monocarboxylic acids, branched saturated monocarboxylic acids and alicyclic monocarboxylic acids. The saturated monocarboxylic acids preferably contains 4 to 20 carbon atoms, more preferably 6 to 20 carbon atoms, particularly preferably 8 to 20 carbon atoms.

The main products resulting from the reaction using saturated monocarboxylic acids as the starting compounds are dicarboxylic acids containing one more carbon atom than the starting saturated monocarboxylic acids, namely dicarboxylic acids with one carboxyl group introduced. The use of the saturated monocarboxylic acids as the starting compounds generally gives saturated carboxylic acids.

Typical but nonlimitative examples of the saturated monocarboxylic acids to be used as the starting compounds are n-pentanoic acid, n-hexanoic acid, n-octanoic acid, n-nonanoic acid, n-decanoic acid, n-undecanoic acid, n-dodecanoic acid, n-tridecanoic acid, n-tetradecanoic acid (myristic acid), n-pentadecanoic acid, n-hexadecanoic acid, n-heptadecanoic acid, n-octadecanoic acid, n-nonadecene and n-icosanoic acid.

Typical but nonlimitative examples of the saturated monocarboxylic esters to be used as the starting compounds are methyl esters and ethyl esters of the above-described saturated monocarboxylic acids.

The main products resulting from the reaction using the saturated monocarboxylic esters as the starting compounds are monocarboxylic acids containing one more carbon atom than the starting saturated monocarboxylic esters, namely carboxy-monocarboxylic esters (monocarboxylic acids) with one carboxyl group introduced. The use of the saturated carboxylic esters as the starting compounds generally gives saturated carboxylic acids.

These various starting compounds may be used individually or as mixtures of two or more, and may also contain impurities or other components than the above-described starting compounds, so far as the object of the present invention can be attained.

An important point of the present invention is to carry out the reaction (the Koch's reaction) of the starting compounds with carbon monoxide in a strong acid solution containing at least trifluoromethane-sulfonic acid catalyst and alcohols and/or olefins of 3 to 5 carbon atoms. If water exists during the reaction in the specific strong acid solution comprising the catalyst and the additives, the reaction products of the saturated hydrocarbons and carbon monoxide may partially undergo hydrolysis with water to form carboxylic acids. However, if water exists in excess, the strong acidity of the catalyst will be impaired so that sufficient activity cannot be exhibited. It is therefore desirable at the stage of the carbonylization by CO to construct a reaction system wherein the water concentration in the reaction solution is maintained low enough relative at least to the trifluoromethane-sulfonic acid.

That is, the concentration of the trifluoromethane-sulfonic acid itself in the reaction solution is not particularly limited, but when the starting compounds are allowed to react with carbon monoxide and water at the same time at atmospheric pressure, the percentage of the trifluoromethane-sulfonic acid based on the total of the trifluoromethane-sulfonic acid and water is preferably at least 92% by weight, particularly preferably at least 96% by weight. If it is less than 92% by weight, the yield of carboxylic acids may be decreased. When alcohols are added as the additives, it is desirable to take the water which will be formed by the dehydration of the alcohols into account.

When saturated monocarboxylic acids or saturated monocarboxylic esters are used as the starting compounds, it is preferable to further use organic solvents, for example, halogenated hydrocarbons, such as dichloromethane, and saturated hydrocarbons, such as n-octane. The amount of the solvents is preferably 1 to 100 times as much as the weight of the starting compounds. Ketones, alcohols, ethers and esters may react with the catalyst.

The alcohols and olefins which are put in contact with the trifluoromethane-sulfonic acid catalyst may have various structures and various carbon numbers, and those of 3 to 8 carbon atoms, particularly 3 to 5 carbon atoms are generally preferable. Alcohols or olefins of 9 or more carbon atoms tend to undergo reactions preferentially, to hinder the desired reaction of saturated hydrocarbons. Alcohols and olefins of not more than two carbon atoms, such as methanol, ethanol and ethylene, cannot activate the starting saturated hydrocarbons sufficiently, and may also retard the desired reaction of saturated hydrocarbons.

The preferred alcohols are, but not limited to, n-propanol, isopropanol, n-butanol, isobutanol, tert-butanol, n-pentanol, isoamyl alcohol, 1-hexanol, 2-hexanol, 1-heptanol, 2-heptanol, 1-octanol and 2-octanol.

The preferred olefins are, but not limited to, propylene, 1-butene, 2-butene, isobutene, 1-pentene, 2-pentene, 2-methyl-1-butene, 2-methyl-2-butene and 3-methyl-1-butene.

Among the alcohols and the olefins of 3 to 5 carbon atoms, the alcohols alone, or the olefins alone, or both may be added to the reaction system. Further, the alcohols and the olefins, which are used as the additives, may be used individually or in combination of two or more, respectively.

The amount of these olefins and alcohols (when both of them or two or more of each are added, the amount means the total of all) is not particularly limited, and is preferably 1 to 50% by weight, particularly preferably 1 to 20% by weight, based on the amount of the catalyst trifluoromethane-sulfonic acid. If the amount is less than 1% by weight, the desired reaction of saturated hydrocarbons with carbon monoxide may become insufficient. In the complete absence of the alcohols and the olefins, the trifluoromethane-sulfonic acid catalyst alone can hardly make the starting compounds undergo the reaction with carbon monoxide. If the total of the olefins and the alcohols is more than 50% by weight based on trifluoromethane-sulfonic acid, the alcohols and the olefins themselves may undergo reactions preferentially, so that the rate of the objective reaction of the starting compounds with carbon monoxide will be insufficient to give a satisfactory yield of carboxylic acids.

The amount (ratio) of the starting compounds is not particularly limited, and the amount of the saturated hydrocarbons is preferably 50 mol % or more, particularly 100 to 10,000 mol %, based on the amount of the coexisting alcohols or olefins (when both of them or two or more of each added, the amount means the total of all). If the amount of the saturated hydrocarbons is less than 50 mol % on the above-described basis, the yield of carboxylic acids may be decreased. The amount of the saturated monocarboxylic acids or the saturated monocarboxylic esters is preferably 200 mol % or less, particularly preferably 50 to 150 mol %, based on the amount of the coexisting alcohols or olefins added (when both of them or two or more of each are added, the amount means the total of all). If the amount of the saturated hydrocarbons is more than 200 mol % on the above-described basis, the yield of carboxylic acids may be decreased.

The temperature of the reaction of the starting compounds with carbon monoxide is, but not limited to, preferably −40° C. to +80° C., particularly preferably −20° C. to +40° C. If the reaction temperature is lower than −40° C., the catalyst will be solidified and cannot exhibit sufficient activity. If the reaction temperature is higher than 80° C., the meltage of carbon monoxide in the reaction solution will be decreased, and the yield of carboxylic acids may be decreased.

The reaction pressure is not particularly limited, but it is preferable to adjust the partial pressure of CO to at least 0.01 MPa, particularly preferably 0.1 MPa to 10 MPa. In general, the purity of carbon monoxide needn't always be so high, but is preferably of the level of industrial or commercial bombs. If the partial pressure of CO is lower than 0.01 MPa, the reaction rate may be insufficient to give a good yield of carboxylic acids. The total pressure of the gaseous phase is not particularly limited, but if it is lower than 0.01 MPa, there may occur, in addition to the above problem, the vaporization of the catalyst or the starting compounds.

After the above-described reaction of the starting compounds with carbon monoxide goes sufficiently to completion, the reaction mixture is mixed with water in accordance with conventional methods to complete the hydrolytic reaction thereof into carboxylic acids. Thus the objective various carboxylic acids or dicarboxylic acids can be synthesized in a good yield.

Thereafter, the separation and recovery of a carboxylic acid, a mixture of carboxylic acids or a solution or composition containing carboxylic acids may be performed by conventional methods. For example, objective monocarboxylic acids and/or dicarboxylic acids of desired purity can be obtained efficiently by conventional separation-purification-recovery techniques, such as solvent extraction, phase separation or the like.

When compounds selected from saturated hydrocarbons, saturated monocarboxylic acids and saturated monocarboxylic esters are used as the starting compounds, and alcohols are used as the additive components to be selected from alcohols and the olefins of 3 to 5 carbon atoms, it is desirable to conduct the reaction of the starting compounds with carbon monoxide in a strong acid solution comprising trifluoromethane-sulfonic acid catalyst, the alcohols and no water, followed by dilution of the reaction mixture with a large quantity of water, for example with 50 to 200% by weight of water based on the trifluoromethane-sulfonic acid, and extraction of the products with organic solvents.

When compounds selected from saturated hydrocarbons, saturated monocarboxylic acid and saturated monocarboxylic esters are used as the starting compounds, and olefins of 3 to 5 carbons atoms are used as the additive components to be selected from the alcohols and the olefins of 3 to 5 carbon atoms, it is desirable to conduct the reaction of the starting compounds with carbon monoxide in a strong acid solution comprising trifluoromethane-sulfonic acid catalyst, the olefins of 3 to 5 carbon atoms and water, followed by dilution of the reaction mixture with a large quantity of water, for example with 50 to 200% by weight of water based on the trifluoromethane-sulfonic acid and extraction of the products with organic solvents. The amount of the water added to the strong acid solution is generally at least equimolar with the olefins of 3 to 5 carbon atoms with the proviso the amount of trifluoromethane-sulfonic acid is preferably 92% by weight or more based on the total of the water and trifluoromethane-sulfonic acid.

Hereinafter, the present invention will be described in more detail referring to Examples and Comparative Examples, but the scope of the present invention is not limited to the Examples.

EXAMPLE 1

In a 200 ml flask was placed 26 g (0.17 moles) of trifluoromethane-sulfonic acid, and while CO gas was blown through the reaction system at 15° C., a 13% by weight IPA (isopropanol) solution in cyclohexane (IPA 0.04 moles, cyclohexane 0.20 moles) was added dropwise over a period of 2 hours, followed by further reaction for one hour. The reaction was conducted at atmospheric pressure (CO partial pressure: 0.1 MPa).

After addition of 26 g of water, the reaction solution was extracted with cyclohexane to obtain carboxylic acids. Analysis showed that the yield of carboxylic acids from the hydrocarbon was 70% and that the main products were 1-methylcyclopentane carboxylic acid and cyclohexane carboxylic acid.

EXAMPLE 2

Reaction and after treatment were carried out in the same manner as in Example 1 except that n-hexane was used in place of cyclohexane.

EXAMPLES 3 TO 6

Reaction and after treatment were carried out in the same manner as in Example 1 except that secondary alcohols of 4 to 7 and 8 carbon atoms were used in place of IPA.

EXAMPLE 7

Reaction and after treatment were carried out in the same manner as in Example 1 except that 27 g (0.17 moles) of 98% trifluoromethane-sulfonic acid was used as a catalyst, and propylene was used in place of IPA.

COMPARATIVE EXAMPLE 1

Reaction and after treatment were carried out in the same manner as in Example 1 except that sulfuric acid was used in place of $CF_3SO_3H$. The yield of carboxylic acids was 5%.

COMPARATIVE EXAMPLE 2

Reaction and after treatment were carried out in the same manner as in Example 1 except that IPA was not used. No carboxylic acids were formed.

EXAMPLES 8 TO 12

In a 200 ml five-necked flask was placed trifluoromethane-sulfonic acid in amounts as listed in table and while CO gas was blown through the reaction system IPA (isopropanol) solutions of the concentration as listed in table in the hydrocarbons as listed in table were added dropwise over a period of 2 hours, followed by further reaction for one hour. The reaction was conducted at 15° C. at atmospheric pressure (CO partial pressure: 0.1 MPa).

After addition of the same weight of water as the catalyst, the reaction solutions were extracted with cyclohexane to obtain extracts. The extracts were analyzed to obtain the yields of dicarboxylic acids and other products.

COMPARATIVE EXAMPLES 3 TO 4

Reaction and after treatment were carried out in the same manner as in Examples 8 to 12 except that 98% sulfuric acid was used in place of the trifluoromethane-sulfonic acid catalyst.

COMPARATIVE EXAMPLE 5

Reaction and after treatment were carried out in the same manner as in Examples 8 to 12 except that IPA was not used.

EXAMPLES 13 TO 16

Reaction and after treatment were carried out in the same manner as in Examples 8 to 12 except that IPA and the monocarboxylic acids as listed in table, both of which were dissolved in n-octane or dichloromethane, were used as the starting compounds.

EXAMPLES 17 TO 18

Reaction and after treatment were carried out in the same manner as in Examples 8 to 12 except that IPA and the monocarboxylic esters as listed in table, both of which were dissolved in n-octane or dichloromethane, were used as the starting compounds.

The results of Examples and Comparative Examples are shown in Tables 1 to 8. In these Examples and Comparative Examples, the yields of carboxylic acids were defined as and calculated by the following equation.

Yield of carboxylic acids (%)={[Total of carboxyl groups formed (moles)]/[Total of alcohols and olefins of 3 to 5 carbon atoms added (moles)]}×100

TABLE 1

| | Starting compounds | | | Yields of carboxylic acid from hydrocarbons | |
| --- | --- | --- | --- | --- | --- |
| | Saturated hydrocarbons | Alcohols or olefins | Catalysts | Monocarboxylic acids | Dicarboxylic acids |
| Example Nos. | | | | | |
| 1 | Cyclohexane | IPA | TRF | 70% | 0% |
| 2 | n-Hexane | IPA | TRF | 67% | 0% |
| 3 | Cyclohexane | 2-Butanol | TRF | 50% | 0% |
| 4 | Cyclohexane | 2-Pentanol | TRF | 36% | 0% |
| 5 | Cyclohexane | 2-Hexanol | TRF | 15% | 0% |
| 6 | Cyclohexane | 2-Octanol | TRF | 5% | 0% |
| 7 | Cyclohexane | Propylene | 98% TRF | 79% | 0% |

TABLE 1-continued

| | Starting compounds | | | Yields of carboxylic acid from hydrocarbons | |
|---|---|---|---|---|---|
| | Saturated hydrocarbons | Alcohols or olefins | Catalysts | Monocarboxylic acids | Dicarboxylic acids |
| Comparative Example Nos. | | | | | |
| 1 | Cyclohexane | IPA | Sulfuric acid | 5% | 0% |
| 2 | Cyclohexane | — | TRF | 0% | 0% |

TRF: trifluoromethane-sulfonic acid
IPA: isopropanol

TABLE 2

| | Starting compounds | | | | Yields of carboxylic acids from hydrocarbons | |
|---|---|---|---|---|---|---|
| | Saturated hydrocarbons | Alcohols | Solvents | Catalysts | Monocarboxylic acids | Dicarboxylic acids |
| Example Nos. | | | | | | |
| 8 | n-Octane 14.0 g (123 mmol) | IPA 2.60 g (43 mmol) | — | TRF 26.4 g (176 mmol) | 62% | 1% |
| 9 | n-Decane 14.5 g (102 mmol) | IPA 2.55 g (42 mmol) | — | TRF 26.9 g (179 mmol) | 43% | 9% |
| 10 | n-Undecane 17.4 g (111 mmol) | IPA 2.53 g (42 mmol) | — | TRF 25.4 g (169 mmol) | 36% | 16% |
| 11 | n-Dodecane 14.9 g (88 mmol) | IPA 2.57 g (43 mmol) | — | TRF 26.4 g (176 mmol) | 20% | 28% |
| 12 | n-Tetradecane 19.2 g (197 mmol) | IPA 2.56 g (43 mmol) | — | TRF 26.8 g (179 mmol) | 8% | 30% |
| Comparative Example Nos. | | | | | | |
| 3 | n-Decane 14.5 g (102 mmol) | IPA 2.54 g (42 mmol) | — | 98% $H_2SO_4$ 18.0 g (180 mmol) | 4% | 0% |
| 4 | n-Dodecane 15.0 g (88 mmol) | IPA 2.55 g (43 mmol) | — | 98% $H_2SO_4$ 18.1 g (181 mmol) | 3% | 0% |
| 5 | n-Decane 14.5 g (102 mmol) | — | — | TRF 26.4 g (176 mmol) | 0% | 0% |

TABLE 3

| | Starting compounds | | | | Yields of carboxylic acids from monocarboxylic acids | |
|---|---|---|---|---|---|---|
| | Monocarboxylic acids | Alcohols | Solvents | Catalysts | | Dicarboxylic acids |
| Example Nos. | | | | | | |
| 13 | n-Nonanoic acid 6.56 g (41 mmol) | IPA 2.55 g (42 mmol) | n-Octane 14.0 g (123 mmol) | TRF 26.5 g (177 mmol) | | 1% |
| 14 | n-Undecanoic acid 7.03 g (38 mmol) | IPA 2.54 g (42 mmol) | n-Octane 14.1 g (123 mmol) | TRF 27.2 g (181 mmol) | | 8% |
| 15 | n-Undecanoic acid 6.98 g (38 mmol) | IPA 2.57 g (43 mmol) | Dichloromethane 26.0 g (306 mmol) | TRF 26.4 g (176 mmol) | | 5% |

TABLE 3-continued

| | Starting compounds | | | | Yields of carboxylic acids from |
|---|---|---|---|---|---|
| | Monocarboxylic acids | Alcohols | Solvents | Catalysts | monocarboxylic acids Dicarboxylic acids |
| 16 | Myristic acid 7.22 g (32 mmol) | IPA 2.47 g (41 mmol) | n-Octane 19.2 g (168 mmol) | TRF 26.3 g (175 mmol) | 12% |

TABLE 4

| | Starting compounds | | | | Yields of carboxylic acids from |
|---|---|---|---|---|---|
| | Monocarboxylic esters | Alcohols | Solvents | Catalysts | monocarboxylic esters monocarboxylic acids |
| Example Nos. | | | | | |
| 17 | Methyl myristate 7.24 g (30 mmol) | IPA 2.60 g (43 mmol) | n-Octane 18.4 g (161 mmol) | TRF 26.8 g (179 mmol) | 9% |
| 18 | Methyl myristate 7.16 g (30 mmol) | IRA 2.63 g (44 mmol) | Dichloromethane 23.1 g (272 mmol) | TRF 26.4 g (176 mmol) | 26% |

TABLE 5

Example 1: Cyclohexane + $CF_3SO_3H$ / IPA, CO → 1-methylcyclopentane-1-carboxylic acid (64%) + cyclohexanecarboxylic acid (6%)

Example 2: n-hexane + $CF_3SO_3H$ / IPA, CO → branched carboxylic acid (50%) + branched carboxylic acid (17%)

Example 3: Cyclohexane + $CF_3SO_3H$ / 2-butanol, CO → 1-methylcyclopentane-1-carboxylic acid (45%) + cyclohexanecarboxylic acid (5%)

Example 4: Cyclohexane + $CF_3SO_3H$ / 2-pentanol, CO → 1-methylcyclopentane-1-carboxylic acid (32%) + cyclohexanecarboxylic acid (4%)

Example 5: Cyclohexane + $CF_3SO_3H$ / 2-hexanol, CO → 1-methylcyclopentane-1-carboxylic acid (13%) + cyclohexanecarboxylic acid (2%)

Example 6: Cyclohexane + $CF_3SO_3H$ / 2-octanol, CO → 1-methylcyclopentane-1-carboxylic acid (5%)

Example 7: Cyclohexane + $CF_3SO_3H$ / propylene, CO → 1-methylcyclopentane-1-carboxylic acid (71%) + cyclohexanecarboxylic acid (8%)

TABLE 6

| | Starting material | Reaction | Product |
|---|---|---|---|
| Example 8 | CH₃(CH₂)₅CH=CH₂ (or alkene) | CF₃SO₃H / IPA, CO | HOOC-C(-)(-)-COOH and others |
| Example 9 | long-chain alkene | CF₃SO₃H / IPA, CO | HOOC-C(-)-CH₂-COOH and others |
| Example 10 | long-chain alkene | CF₃SO₃H / IPA, CO | branched dicarboxylic acid COOH and others |
| Example 11 | long-chain alkene | CF₃SO₃H / IPA, CO | HOOC-branched-COOH and others |
| Example 12 | long-chain alkene | CF₃SO₃H / IPA, CO | HOOC-branched-COOH and others |
| Example 13 | alkyl-COOH | CF₃SO₃H / IPA, CO | HOOC-branched-COOH and others |
| Examples 14–15 | alkyl-COOH | CF₃SO₃H / IPA, CO | HOOC-branched-COOH and others |
| Example 16 | long alkyl-COOH | CF₃SO₃H / IPA, CO | HOOC-branched-COOH and others |
| Examples 17–18 | alkyl-COOCH₃ | CF₃SO₃H / IPA, CO | HOOC-branched-COOCH₃ and others |

According to the present invention, various carboxylic acids are prepared by a novel reaction technique of conducting the Koch's reaction of compounds selected from saturated hydrocarbons, saturated monocarboxylic acids and saturated monocarboxylic esters with carbon monoxide using a catalyst system which is a specific combination of trifluoromethane-sulfonic acid catalyst, which alone has no activity in the Koch's reaction of saturated hydrocarbons, with alcohols and/or olefins. By the novel reaction technique, a good yield of monocarboxylic acids and/or dicarboxylic acids can be synthesized even under mild conditions at around atmospheric pressure and at around room temperature, even from compounds containing saturated hydrocarbon groups with no tertiary hydrogen atoms, such as straight-chain alkanes and cyclohexane, which have been known to be hardly applicable with catalysts or catalyst systems other than extremely corrosive magic acids, such as HF-SbF₅.

To the production of carboxylic acids by the Koch's reactions of compounds containing saturated hydrocarbons with tertiary hydrogen atoms, the process of the present invention is also advantageous as compared with the conventional processes using sulfuric acid catalysts, since the catalyst system containing no sulfuric acid does not cause the contamination of the product carboxylic acids with sulfur which emits offensive odor.

Industrial Applicability

According to the process of the present invention, monocarboxylic acids and/or dicarboxylic acids of much practical use can be obtained in a good yield by the Koch's reaction of not only saturated hydrocarbons, saturated monocarboxylic acids and saturated monocarboxylic esters which have tertiary hydrogen atoms, but also those containing alkyl groups with no tertiary hydrogen atoms, even under mild conditions at around atmospheric pressure and at around room temperature.

We claim:

1. A process for producing a monocarboxylic acid and/or a dicarboxylic acid by a reaction of a starting compound selected from the group consisting of a saturated hydrocarbon, a saturated monocarboxylic acid and a saturated monocarboxylic ester either with both of carbon monoxide and water at the same time or first with carbon monoxide and then with water, wherein the reaction of the starting compound either with both of carbon monoxide and water or with carbon monoxide alone is conducted in a strong acid solution containing at least trifluoromethane-sulfonic acid catalyst and an alcohol and/or an olefin of 3 to 5 carbon atoms.

2. The process of claim 1, wherein the product monocarboxylic acid and/or the product dicarboxylic acid is a monocarboxylic acid containing one more carbon atom than the starting compound and/or a dicarboxylic acid containing two more carbon atoms than the starting compound.

3. The process of claim 2, wherein the saturated hydrocarbon is used as the starting compound, to produce a monocarboxylic acid containing one more carbon atom than the starting compound and/or a dicarboxylic acid containing two more carbon atoms than the starting compound.

4. The process of claim 2, wherein the saturated monocarboxylic acid is used as the starting compound, to produce a saturated dicarboxylic acid containing one more carbon atom than the starting compound.

5. The process of claim 2, wherein the saturated monocarboxylic ester is used as the starting compound, to prepare a saturated monocarboxylic acid containing one more carbon atom than the starting compound.

6. The process of claim 1, wherein the starting compound selected from the group consisting of the saturated hydrocarbon, the saturated monocarboxylic acid and the saturated monocarboxylic ester contains an alkyl chain containing no tertiary hydrogen atoms.

7. The process of claim 1, wherein the alcohol has 3 to 8 carbon atoms.

8. The process of claim 7, wherein the alcohol has 3 to 5 carbon atoms.

9. The process of claim 1, wherein the saturated hydrocarbon and the saturated monocarboxylic acid contain 4 to 20 carbon atoms.

10. The process of claim 1, wherein the saturated hydrocarbon and the saturated monocarboxylic acid contain 8 to 20 carbon atoms.

11. The process of claim 1, wherein the starting compound is selected from the group consisting of the saturated hydrocarbon, the saturated monocarboxylic acid and the saturated monocarboxylic ester, and the reaction of the starting compound with carbon monoxide is carried out in a strong acid solution which comprises the trifluoromethane-sulfonic acid catalyst and the alcohol and contains no water.

12. The process of claim 11, wherein the starting compound is the saturated hydrocarbon, the saturated hydrocarbon is used in an amount of 100 to 10,000 mol % based on the alcohol, the alcohol is used in an amount of 1 to 50% by weight based on the trifluoromethane-sulfonic acid catalyst, and the reaction in the strong acid solution is carried out at an atmospheric pressure with a partial pressure of carbon monoxide of 0.1 to 10 MPa.

13. The process of claim 11, wherein the starting compound is the saturated monocarboxylic acid or the saturated monocarboxylic ester, the saturated monocarboxylic acid or the saturated monocarboxylic ester is used in an amount of 50 to 150 mol % based on the alcohol, the alcohol is used in an amount of 1 to 50% by weight based on the trifluoromethane-sulfonic acid catalyst, and the reaction in the strong acid solution is carried out at atmospheric pressure with a partial pressure of carbon monoxide of 0.1 to 10 MPa.

14. The method of any one of claims 11 to 13, wherein 50 to 200% by weight of water based on the trifluoromethane-sulfonic acid is added to a reaction mixture resulting from the reaction in the strong acid solution, to form the product monocarboxylic acid and/or the product dicarboxylic acid, which is then extracted with a solvent.

* * * * *